United States Patent [19]

Gruteser

[11] Patent Number: 5,137,831
[45] Date of Patent: Aug. 11, 1992

[54] METHOD FOR THE CONTINUOUS DETERMINATION OF DIMETHYLFORMAMIDE AND DIMETHYLAMINE IN AQUEOUS SOLUTIONS, ESPECIALLY IN EFFLUENTS

[75] Inventor: Rudolf Gruteser, Kelheim, Fed. Rep. of Germany

[73] Assignee: Hoechst Aktiengesellschaft, Frankfurt am Main, Fed. Rep. of Germany

[21] Appl. No.: 595,206

[22] Filed: Oct. 10, 1990

[30] Foreign Application Priority Data

Oct. 12, 1989 [DE] Fed. Rep. of Germany ....... 3934025

[51] Int. Cl.$^5$ ..................... G01N 25/14; G01N 27/00
[52] U.S. Cl. ..................... 436/52; 436/106; 436/111; 436/181
[58] Field of Search .............. 436/52, 106, 111, 150, 436/181

[56] References Cited
PUBLICATIONS

Houben-Weyl, "Methoden der Organischen Chemie", Physikalische Methoden, vol. 3, part 2, p. 8, 1955.

Primary Examiner—David L. Lacey
Assistant Examiner—David Redding
Attorney, Agent, or Firm—Connolly and Hutz

[57] ABSTRACT

Method for the continuous determination of dimethylformamide and dimethylamine in aqueous solutions, especially in effluents. A method for the continuous determination of the amount of dimethylformamide in a solution containing dimethylformamide, the amount of dimethylamine in a solution containing dimethylamine, and the combined amount of dimethylformamide and dimethylamine in a solution contained in aqueous solutions, especially in plant effluents, is described, which comprises continuously taking a constant part stream from the effluent stream, hydrolyzing the part stream under alkaline conditions with an alkali solution added at a constant rate under constant conditions, subjecting it to partial vaporization conditions, condensing the resulting vapor stream by cooling, determining the electrical conductivity in the condensate continuously in a flow cell and converting the measured values obtained into the desired concentration values by reference to a calibration curve or known equations.

9 Claims, 2 Drawing Sheets

METHOD FOR THE CONTINUOUS DETERMINATION OF DIMETHYLFORMAMIDE AND DIMETHYLAMINE IN AQUEOUS SOLUTIONS, ESPECIALLY IN EFFLUENTS

Method for the continuous determination of dimethylformamide and dimethylamine in aqueous solutions, especially in effluents.

INTRODUCTION

The present invention relates to a method for the quantitative determination of dimethylformamide and/or dimethylamine in aqueous solutions, in particular in continuously arising solutions such as, for example, in effluents. Aqueous solutions, in particular effluents, which contain small quantities of dimethylformamide and dimethylamine, arise in many fields of industry.

BACKGROUND OF THE INVENTION

Owing to its small molecular size, its dielectric constant, its electron donor properties and its ability to form complexes, dimethylformamide is outstandingly suitable as a solvent, especially for high-molecular compounds. It is therefore one of the few solvents suitable for the preparation of spinnable polyacrylonitrile solutions, but the use of dimethylformamide as solvent is also indispensable in the synthetic leather industry and coating industry for the preparation of polyurethane systems for high-quality surfaces. Certain polyamides, especially fully aromatic polyamides, can be spun only in the form of their solutions in DMF or similar solvents.

Owing to its selective solvent power for certain hydrocarbons and gases, dimethylformamide is used in a number of large-scale industrial processes. Thus, for example, acetylene can advantageously be extracted by means of DMF even from cracking gases low in acetylene, and acetylene-free ethylene can be obtained simultaneously.

In the last few years, DMF has even been used as a selective absorbent for butadiene from the $C_4$ fraction of cracking gases. In the petroleum industry, it is used as a selective extractant for aromatics from hydrocarbon mixtures, and for the desulfurization of diesel oils and lubricating oils, and the outstanding solvent and extraction properties of DMF for vitamins, hormones, sulfonamides and antibiotics are also exploited in the pharmaceutical industry.

DMF thus represents an irreplaceable auxiliary in a multiplicity of large-scale industrial processes.

In the event of faults in plant operation or also during certain operating conditions close to the limits of these processes, small or very small quantities of dimethylformamide or its hydrolysis product dimethylamine can pass into the effluent from these production processes and must then be removed from these for ecological reasons. However, this necessity presupposes unbroken monitoring, as far as possible, of the concentration of dimethylformamide and dimethylamine in the plant effluents. For this purpose, an analysis method, which can be handled as easily as possible and gives quick results, for the determination of dimethylformamide and dimethylamine in aqueous solutions is required.

In the past, the hydrolysis with acid has proven itself in particular as a specific method for the determination of dimethylformamide in aqueous solutions. The dimethylamine formed is then separated by distillation from an alkaline solution and nitrosated, and the resulting nitroso compound is determined polarographically. Although this analysis method is relatively accurate, it is too time-consuming and involved for continuous checking of plant effluents.

An example of a further commonly used method for detecting or also for checking the purity of dimethylformamide is gas chromatography. This method also presupposes frequent taking of individual samples and analysis of the latter, and is therefore not really suitable for continuous effluent monitoring. A further known method, which has a low detection limit, is easy to apply and gives rapid and accurate results, is based on the measurement of the electrical conductivity of aqueous solutions containing dimethylamine. However, even this measurement principle has hitherto been used only for the discontinuous determination of the dimethylamine concentration in aqueous solutions. The conventional sample preparation requires the presence of individual samples and presupposes that other substances which conduct electric current are absent.

SUMMARY OF THE INVENTION

It has now been found, surprisingly, that the measurement of the electrical conductivity can also be employed as the measurement principle for a continuous method for the determination of the concentrations of dimethylformamide and dimethylamine in aqueous solutions, especially in plant effluents, when adhering to a combination of process conditions within defined limits.

The present invention thus relates to a method for the continuous determination of dimethylformamide and/or dimethylamine in aqueous solutions, especially in plant effluents, which comprises continuously taking a constant part stream from the effluent stream, hydrolyzing the part stream by means of an alkali solution added at a constant rate under constant conditions, subjecting it to partial vaporization under constant vaporization conditions, condensing the resulting vapor stream by cooling, determining the electrical conductivity in the condensate continuously in a measurement and flow cell and converting the measured values into the desired concentrations, for example by reference to a calibration curve.

The term constant conditions refers to the adding of alkali solution so that the alkali concentration is kept constant as by adding to the effluent stream at such a constant rate that a constant alkali concentration in the mixture results, as described in greater detail below. The term constant vaporization conditions refers to the rate of evaporation that is carried out as related to the stirring speed of evaporation vessel contents, the level of contents and the heating of contents, as described in greater detail below.

DETAILED DESCRIPTION

Figure 1:
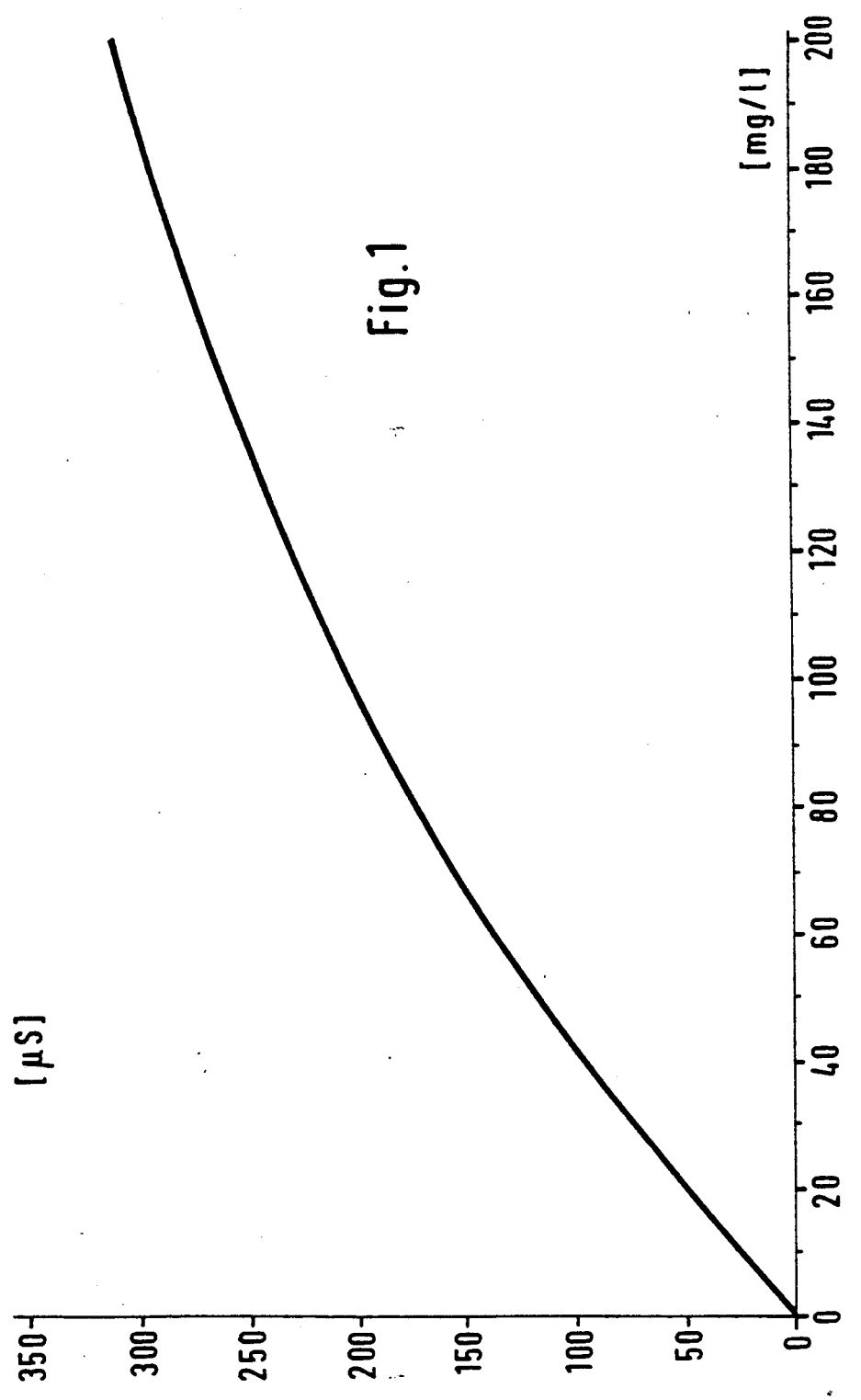
FIG. 1 is a graphical plot of the relationship between the conductivity in microsiemens of the solution to be measured in a flow cell of a measuring apparatus of this invention and the dimethylamine concentration (in mg/l)

To ensure that reproducible measured results are obtained, it is important to keep certain parameters of the method constant within narrow limits, once selected. Thus, it is appropriate to carry out the hydrolysis of the part stream at a selected constant temperature between 70° C. and 100° C., preferably between 85° C. and 95° C. To ensure that this temperature is in fact maintained constant from the start of the hydrolysis up to its end, it is particularly advantageous when the part stream branched off from the effluent stream and expediently also the alkali solution added to the part stream are preheated to the desired hydrolysis temperature.

Alkali solutions which can be used for the hydrolysis are not restricted to alkali metal compounds showing a basic reaction, but in principle all solutions, in particular aqueous solutions, of sufficiently strong bases can be used. For economic and ecological reasons, it is particularly advantageous when the alkali solutions employed are aqueous solutions of alkali metal salts showing a basic reaction, in particular aqueous alkali metal hydroxide solutions. Solutions of sodium hydroxide or potassium hydroxide, in particular those having a high concentration of the alkali metal compound, are particularly preferred for this purpose.

The alkali solution is added to the constant effluent part stream at such a constant rate that a constant alkali concentration in the range from 0.1 to 2.5, preferably 0.25 to 1.25, especially 0.5 to 0.9, g-equivalents per liter results in the mixture.

The alkali concentration is here to be understood as the calculated alkali concentration which results if the quantity of added alkali were mixed with a quantity of pure water equal to the quantity of the part stream.

As already stated above, a partial vaporization of the effluent part stream, which has been rendered alkaline, is to be carried out under constant conditions. To set these constant vaporization conditions, the vaporization is advantageously carried out in a vaporization vessel, in which the contents are stirred at a constant speed and in which the level is kept constant. Advantageously, the heating output of the vaporizer is also kept constant within narrow limits, once selected.

The level in the vaporizer is kept at a constant height by taking off the vaporizer content at a constant control rate from the bottom of the vaporization vessel at the constant rate of distillation resulting from the constant heat supply.

The condensate obtained in the vaporization and condensation of the hydrolysate is, for measuring its electrical conductivity, advantageously fed to a known measuring and flow cell at a constant temperature which is between 5° C. and 50° C. Advantageously, the measuring cell itself is here thermostatically controlled. In place of a very accurate temperature constancy in the measurement of the electrical conductivity, or as a supplement thereto, the measuring cell can be fitted with a temperature-compensated conductivity measurement circuit.

The electrical conductivity L of the distillate depends on the dimethylamine concentration c present therein and on a constant K determined by the measuring arrangement:

$$L = L'(c, K).$$

If all the measurements are carried out by means of one measurement arrangement, once selected, the relationship simplifies to $$L = L'(c).$$

This relationship is advantageously determined once and for all for the substance to be measured, that is to say dimethylamine in this case, by means of a calibration curve.

As noted above FIG. 1 illustrates such a calibration curve which reproduces the relationship between the conductivity measured in microsiemens ($\mu$S) measured in the measuring and flow cell and the dimethylamine concentration in the distillate flowing through the measuring and flow cell.

The evaluation of the measured conductivity values is, however, not at all restricted to the use of a calibration curve, even though this is the simplest possibility. Alternatively, a mathematical equation, representing the calibration curve and derived from the points of the curve, can also be utilized for converting the conductivity values to concentration values. If an electronic computer is used, the measured values can then be output immediately as concentration values. A calculation of the concentration from the measured equivalent conductivity G and the resistance capacity of the measuring and flow cell with the aid of known simple empirical equations, such as are to be found, for example, in Houben-Weyl, "Methoden der Organischen Chemie [Methods of organic chemistry]" (1955) vol. 3, "Physikalische Methoden [Physical methods]", part 2, page 8, is of course possible once the empirical physical constants contained in the equations have been determined for the dimethylamine which is to be measured.

The above invention is explained in greater detail in the following description taken together with the attached drawings.

The present invention also relates to an apparatus (FIG. 2) for carrying out the analytical method described above. The apparatus according to the invention comprises a metering pump (2) with an inlet (1), connected to the suction side, for the part stream to be taken from the main stream of the liquid which is to be analyzed, a preheating unit (3) connected to the delivery side of the metering pump (2) and held at a constant hydrolysis temperature, a mixing section (4) which is connected to the outlet of this unit and into which an inlet (5) leads to which an alkali solution stock vessel (7), which can be heated under control and is adjustable to a constant temperature, is connected via the metering pump (6), a vaporizer (10) connected to the outlet of the mixing section and provided with power-controlled stirring (8) and heating (9) devices and having a bottom outlet (11) with a controlled outflow valve (12), which allows controlled outflow of the vaporizer content, and having a vapor outlet (13), a descending condenser (14) connected to the vapor outlet and measuring and flow cell (15) connected to the outlet thereof, and also the associated indicating and computing unit (16).

The metering pumps present in the measuring arrangement according to the invention can in principle be of any known type, as long as the pump material is not significantly attacked, or not at all, by the liquids to be delivered. Controllable hose pumps have proven particularly suitable in use in practice.

The controlled outflow valve, installed in the bottom outlet of the vaporizer, can also be of any known design but, in particular, here again metering pumps, especially hose pumps, can be used for controlling the outflow.

The descending cooler connected to the vapor outlet of the vaporizer is here to be understood as a condenser in which the condensate no longer runs back into the vessel, but is fed quantitatively to the conductivity flow cell connected thereto.

Figure 2:
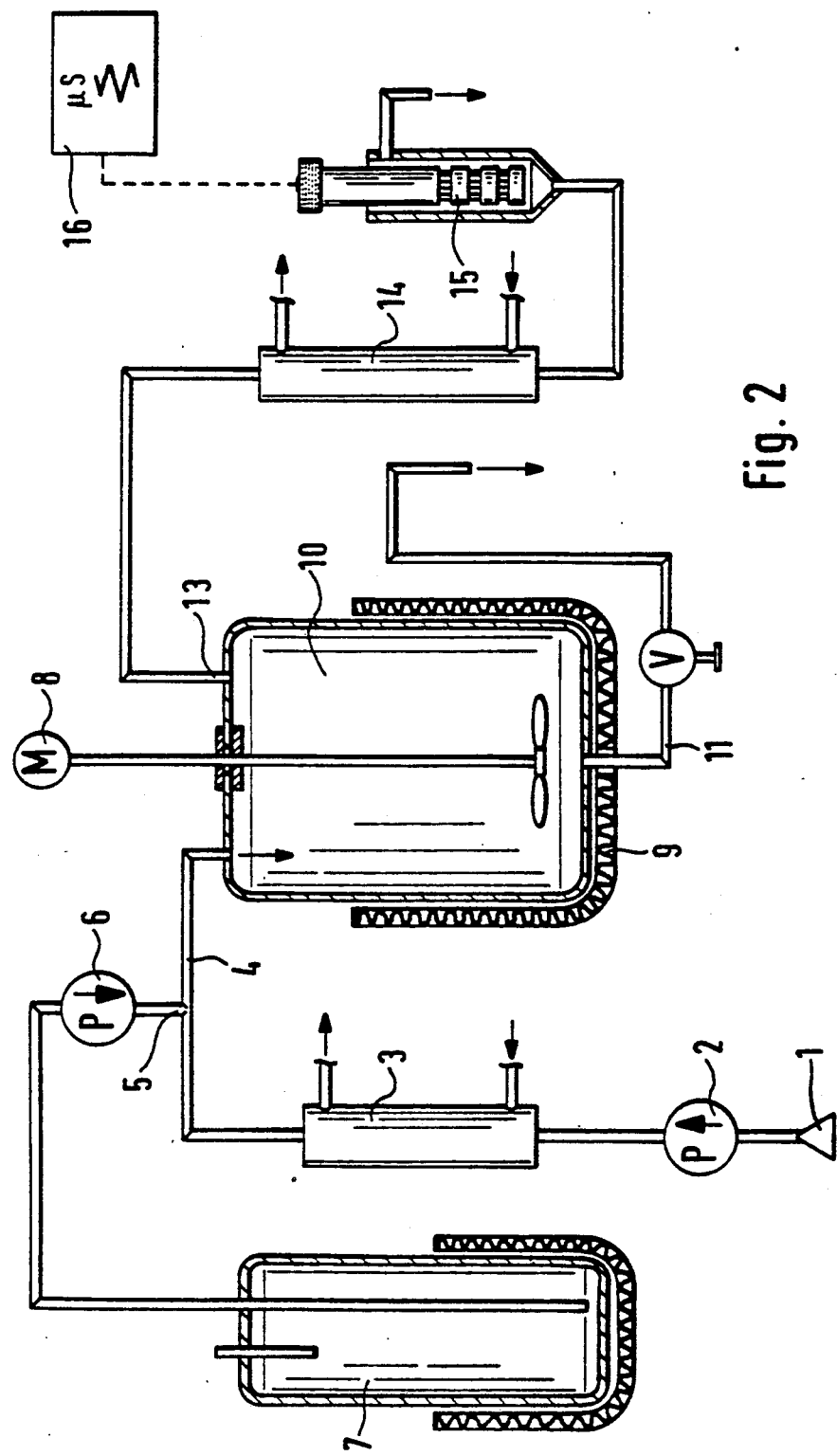
FIG. 2 is a schematic representation of a measuring apparatus of this invention.

The following is a description of an embodiment of the structure of the measuring apparatus of the present invention as illustrated in FIG. 2.

It has proven to be particularly advantageous to fit the vaporizer (10) or a tube communicating with it with a level sensor. This sensor can emit an analog value for the level, or a limit. Advantageously, this level sensor is interconnected with the metering pumps (2) and (6), the outflow controller at the bottom outlet of the vaporizer and the heating element of the vaporizer in such a way that the output of these components can be influenced by the level signal in the direction of keeping the level constant.

For special measuring tasks, it can also be advantageous to insert a rectifying head between the vaporizer and the descending condenser. If desired, such a head can also be provided at several points with connections for taking off various fractions, which are evaluated by separate descending condensers and separate electrical conductivity measuring cells connected thereto.

The method according to the invention is outstandingly suitable for the continuous determination of even small concentrations of dimethylformamide or dimethylamine in aqueous liquid, especially in plant effluents.

A particular advantage of the measurement method according to the invention is that the presence of salts or other strong electrolytes in the liquids to be measured does not interfere with its results. When carrying out the method, it is merely necessary to ensure that, for the case that the aqueous solutions to be measured contain major quantities of carbon dioxide, the quantity of alkali added in the method is such that the carbon dioxide is also retained in the form of carbonates in the vaporizer. A further decisive advantage of the measurement method according to the invention is that every change in the concentration of dimethylformamide or dimethylamine in the aqueous liquids to be measured is indicated with a very short time delay. This means that it is possible to accomplish, on the basis of the measured results, a very effective control of the conditions in the production processes from which the measured effluents originate.

The method according to the invention, which has been described above essentially for the determination of dimethylformamide and dimethylamine in aqueous solutions, can of course readily be employed for the determination of the concentration of other water-soluble acid amides and amines in aqueous solutions, with adaptation of the hydrolysis conditions, provided that the corresponding amines are sufficiently volatile with steam.

I claim:

1. A method for the continuous determination of the amount of dimethylformamide in a solution of dimethylformamide or of the amount of dimethylamine in a solution containing dimethylamine or the combined amount of dimethylformamide and dimethylamine in a solution containing dimethylformamide and dimethylamine, in aqueous solutions, which comprises continuously taking a constant part stream from a continuous stream of said aqueous solution containing said dimethylformamide or said dimethylamine or said dimethylformamide and said dimethylimine, hydrolyzing the part stream under alkaline conditions by means of an alkali solution added at a constant rate and subjecting said part stream to partial vaporization under a constant rate of vaporization, to produce a resulting vaporization stream, condensing the resulting vapor stream to a condensate by cooling, determining the electrical conductivity in the condensate continuously in a measurement flow cell and converting the measured values of the electrical conductivity thus obtained into the desired concentration values of said dimethylformamide or said dimethylamine or said dimethylformamide and said dimethylamine in said aqueous solution.

2. The method as claimed in claim 1, wherein the part stream is hydrolyzed under alkaline conditions at a constant temperature which is between 70° C. and 100° C.

3. The method as claimed in claim 1, wherein the temperature of said hydrolysis of said part stream is adjusted by preheating the part stream and the alkali solution before they are combined.

4. The method as claimed in claim 1, wherein the alkali solution is added to the part stream to produce a mixture at a rate which results in a constant alkali concentration in the range from 0.1 to 2.5 g-equivalents per liter in the mixture.

5. The method as claimed in claim 1, wherein the alkali solution added at a constant rate is an alkali metal hydroxide solution.

6. The method as claimed in claim 1, wherein said vaporization is carried out in an evaporation vessel in which the contents are stirred at a constant speed and in which vaporizer the level of said contents and the heat output of the vaporizer are kept constant.

7. The method as claimed in claim 1, wherein the condensate is fed to the measurement flow cell at a constant temperature between 5° C. and 50° C. and said measurement flow cell is thermostatically controlled.

8. The method as claimed in claim 1, wherein the electrical conductivity is measured by means of a temperature-compensated conductivity measurement circuit.

9. The method as claimed in claim 1, wherein said aqueous solution is an industrial effluent.

* * * * *